(12) United States Patent
Copland

(10) Patent No.: US 11,751,763 B2
(45) Date of Patent: Sep. 12, 2023

(54) METHOD AND SYSTEM FOR PUPIL RETRO ILLUMINATION USING SAMPLE ARM OF OCT INTERFEROMETER

(71) Applicant: AMO Development, LLC, Santa Ana, CA (US)

(72) Inventor: Richard J. Copland, Albuquerque, NM (US)

(73) Assignee: AMO Development, LLC, Irvine, CA (US)

( * ) Notice: Subject to any disclaimer, the term of this patent is extended or adjusted under 35 U.S.C. 154(b) by 92 days.

(21) Appl. No.: 17/103,849

(22) Filed: Nov. 24, 2020

(65) Prior Publication Data

US 2021/0076935 A1    Mar. 18, 2021

Related U.S. Application Data

(62) Division of application No. 15/908,098, filed on Feb. 28, 2018, now Pat. No. 10,849,493.

(Continued)

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0025* (2013.01); *A61B 3/10* (2013.01); *A61B 3/101* (2013.01);
(Continued)

(58) Field of Classification Search
CPC ......... A61B 3/102; A61B 3/0025; A61B 3/10; A61B 3/1005; A61B 3/101; A61B 3/107; A61B 3/14; A61B 5/0066
(Continued)

(56) References Cited

U.S. PATENT DOCUMENTS 5,777,719 A    7/1998  Williams et al.
5,968,095 A   10/1999  Norrby
(Continued)

FOREIGN PATENT DOCUMENTS

WO    2012129508 A1    9/2012
WO    2017019117 A1    2/2017

OTHER PUBLICATIONS

International Search Report and Written Opinion for Application No. PCT/US2018/020250, dated May 22, 2018, 10 pages.
(Continued)

*Primary Examiner* — James R Greece
(74) *Attorney, Agent, or Firm* — Johnson & Johnson Surgical Vision, Inc.

(57) ABSTRACT

An optical measurement instrument includes optical coherence tomography (OCT) interferometer and a pupil retro illumination system which directs laser light onto the retina of an eye via the sample arm of the OCT interferometer. The laser light passes through an intraocular lens (IOL) implanted into the eye, and an iris camera captures an image of the eye from a portion of the light returned from the retina of the eye, the returned light also passing through the IOL. One or more fiducials of the IOL are detected from the captured image, and an angular orientation of the eye is ascertained from the one or more detected fiducials.

13 Claims, 12 Drawing Sheets

Related U.S. Application Data

(60) Provisional application No. 62/465,074, filed on Feb. 28, 2017.

(51) Int. Cl.
*A61B 5/00* (2006.01)
*A61B 3/14* (2006.01)
*A61B 3/107* (2006.01)
*G01B 9/02017* (2022.01)
*G01B 9/02* (2022.01)

(52) U.S. Cl.
CPC ............ *A61B 3/1005* (2013.01); *A61B 3/107* (2013.01); *A61B 3/14* (2013.01); *A61B 5/0066* (2013.01); *G01B 9/02017* (2013.01); *G01B 9/02083* (2013.01)

(58) Field of Classification Search
USPC ........................................ 351/205, 221, 246
See application file for complete search history.

(56) References Cited

U.S. PATENT DOCUMENTS

| | | | |
|---|---|---|---|
| 6,550,917 | B1 | 4/2003 | Neal et al. |
| 7,980,699 | B2 | 7/2011 | Neal et al. |
| 8,087,782 | B2 | 1/2012 | Norrby |
| 2009/0161090 | A1* | 6/2009 | Campbell .............. G01B 11/25 351/212 |
| 2011/0118609 | A1 | 5/2011 | Goldshleger et al. |
| 2011/0292340 | A1 | 12/2011 | Shimizu et al. |
| 2014/0104576 | A1 | 4/2014 | Bor et al. |
| 2014/0368793 | A1 | 12/2014 | Friedman et al. |
| 2015/0018674 | A1 | 1/2015 | Scott et al. |
| 2015/0031993 | A1 | 1/2015 | Buckland et al. |
| 2016/0054116 | A1* | 2/2016 | Khomenko ............... G01L 1/24 356/497 |
| 2016/0150952 | A1* | 6/2016 | Raymond ........... A61F 9/00829 351/205 |
| 2017/0027437 | A1 | 2/2017 | Neal et al. |
| 2019/0223714 | A1 | 7/2019 | Raymond et al. |

OTHER PUBLICATIONS

Mejia-Barbosa Y., et al., "Object Surface For Applying A Modified Hartmann Test To Measure Corneal Topography," Applied Optics, Nov. 1, 2001, vol. 40 (31), pp. 5778-5786.

* cited by examiner

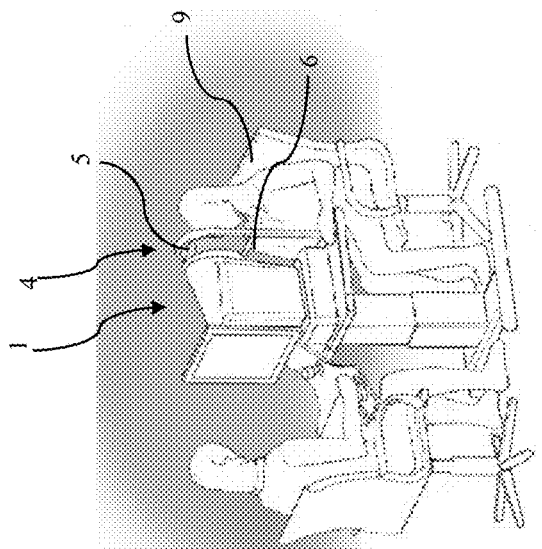
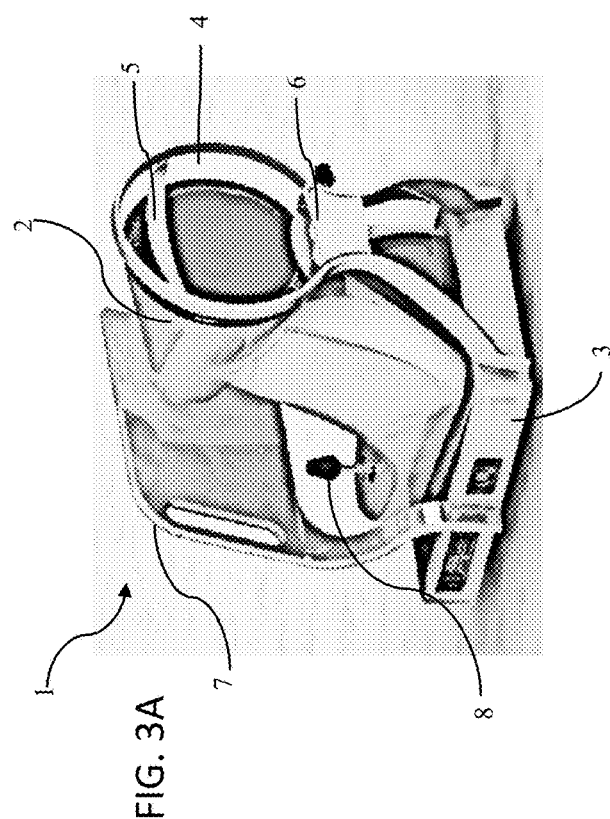
FIG. 3A
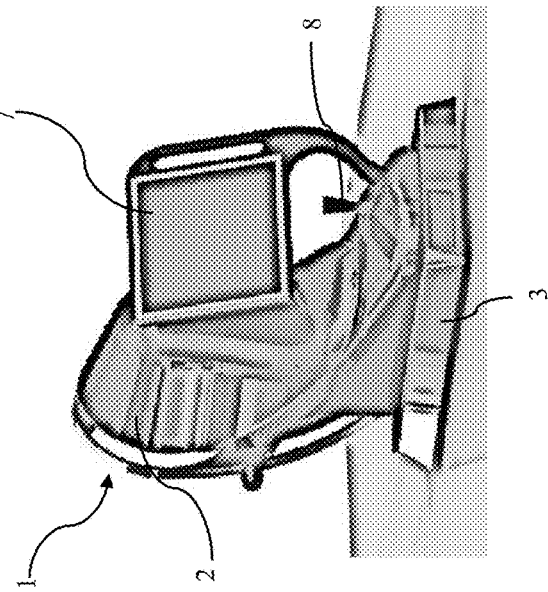
FIG. 3B
FIG. 3C

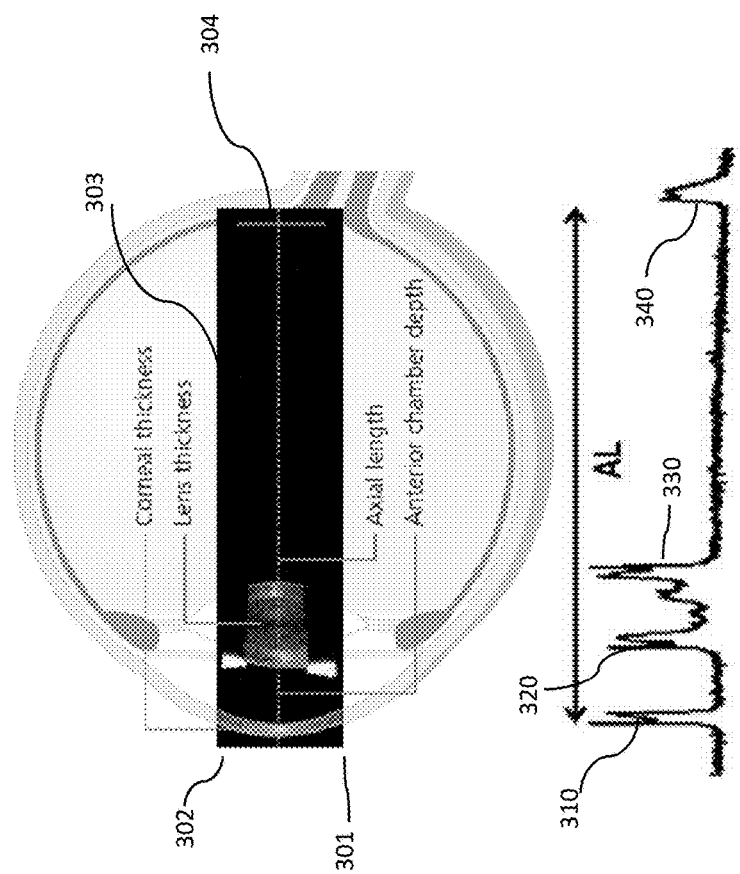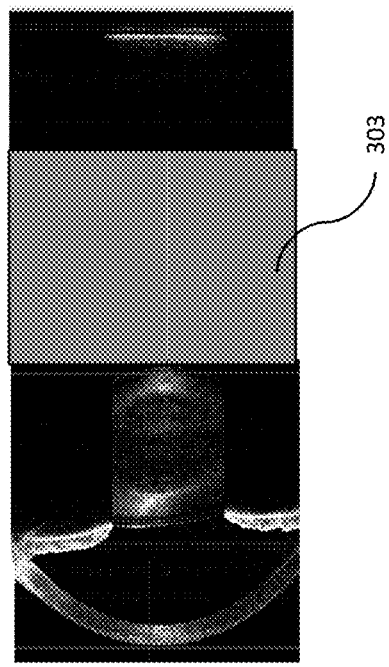
FIG. 8A
FIG. 8B
FIG. 8C

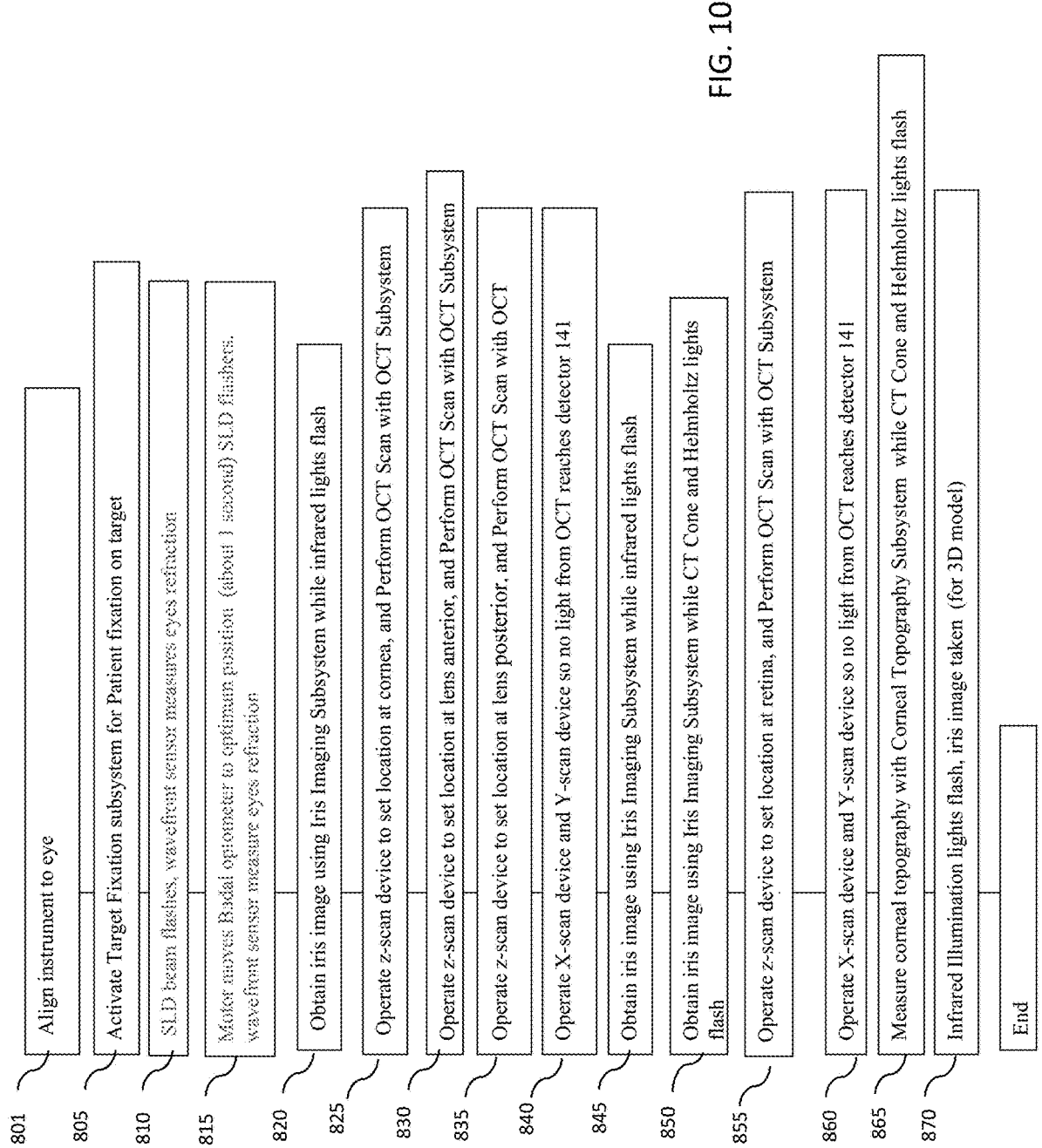

METHOD AND SYSTEM FOR PUPIL RETRO ILLUMINATION USING SAMPLE ARM OF OCT INTERFEROMETER

This application claims priority to U.S. patent application Ser. No. 15/908,098, filed Feb. 28, 2018, which claims priority to U.S. Provisional Patent Application No. 62/465,074, filed on Feb. 28, 2017, all of which are incorporated herein by reference in their entirety.

TECHNICAL FIELD

Embodiments of this invention pertain to optical measurement systems and methods, and more particularly, to optical measurement systems and methods which employ pupil retro illumination to ascertain the angular orientation of an implanted intraocular lens (IOL) in an eye.

BACKGROUND

After implantation of an intraocular lens (IOL), and particularly a toric IOL, it is desired to be able to determine the orientation of the IOL, and particularly the angular orientation within the eye, for example to determine if the IOL has rotated from the desired angular orientation after surgery, for example due to settling which may occur during healing that occurs. In particular, after a patient has had a toric IOL implanted, if the patient's resultant vision is not as good as expected, if may be desirable for a physician to be able to determine if the issue was caused by the selection of an IOL with a non-optimal refraction, or if the toric IOL has rotated relative to its intended orientation within the eye.

Also, it is desired to make objective measurements of the eye after implantation of a toric IOL, and beneficially also before the implantation, to objectively assess the results of the implantation, and preferably in a case where less than optimal results are achieved, to diagnose the reasons for such results. Such measurements may include the refraction, the magnitude of the astigmatism of the eye with the implanted IOL and its axis, and the depth pf the IOL within the eye. The depth of the IOL in the eye affects the magnitude of the astigmatism correction the IOL provides. It would be beneficial if the IOL orientation and refractive cylinder axis could be measured using the same instrument at the same instant, or nearly the same instant, in time as each other, to produce more reliable results.

A wavefront aberrometer may be employed to measure the refraction, astigmatism, axis, and higher order aberrations of a subject's eye using infrared light, and optical coherence tomography (OCT) may be employed to measure the distances between different surfaces within an eye. Various types of OCT are known, including Fourier domain optical coherence tomography (FD-OCT), which in turn includes spectral domain optical coherence tomography (SD-OCT) and swept-source OCT (SS-OCT), and any of these may be employed.

Accordingly, it would be desirable to provide a single measurement instrument which is capable of making wavefront measurements, making OCT measurements, and determining the angular orientation of an implanted toric IOL in an eye. Other methods of measuring anterior chamber depth (ACD) would be similarity advantageous such as Purkinje image analysis. It would also be desirable to provide such an instrument which has a minimal complexity and componentry, especially any expensive componentry. It would further be desirable to provide a method of making wavefront measurements, making OCT measurements, and determining the angular orientation of an implanted toric IOL in an eye with a single instrument.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIG. 3A illustrates a front perspective view showing an optical measurement system according to many embodiments.

FIG. 3B illustrates a rear perspective view showing an optical measurement system according to many embodiments.

FIG. 3C illustrates a side perspective view showing an optical measurement system according to many embodiments.

FIG. 8A illustrates a preferred scanning region for the OCT subsystem according to many embodiments of the present invention.

FIG. 8B shows a representative graph of an intensity of an OCT signal of an OCT subsystem according to many embodiments as a function of depth along the axis defining the axial length of the eye.

FIG. 8C shows a cross-section of an eye obtained by an optical measurement system of the present invention using an OCT subsystem according to the present invention

FIG. 10 is a flowchart of an example embodiment of a method for measuring one or more characteristics of an eye, including wavefront aberrometry, corneal topography and OCT measurements at various locations with the eye along the axial length of the eye.

DETAILED DESCRIPTION

Figure 1A:
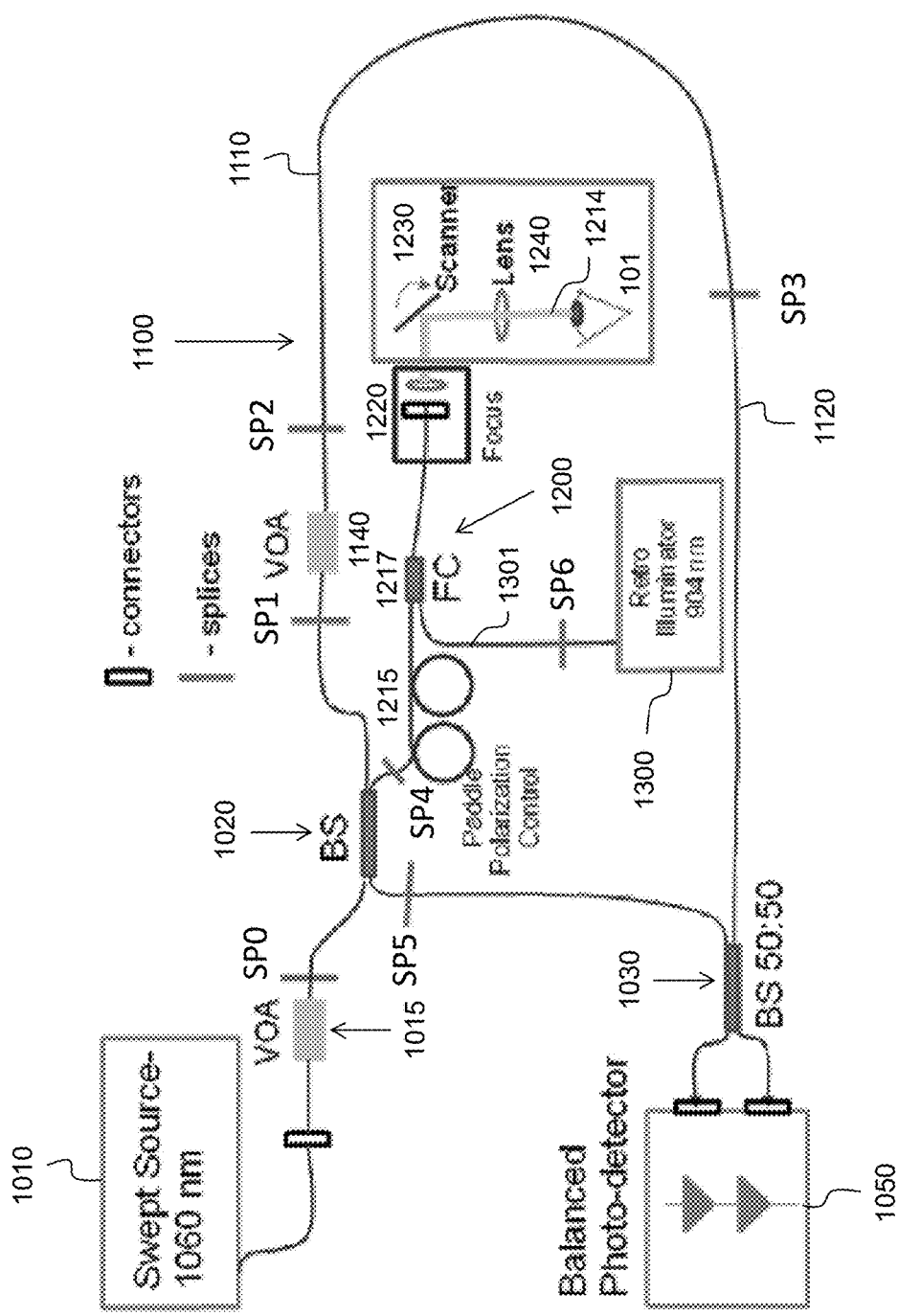
FIG. 1A illustrates an example embodiment of an optical coherence tomography (OCT) interferometer which provides pupil retro illumination via its sample arm.

Exemplary embodiments of optical measurement systems and methods for measuring aberrations of an eye to illustrate various aspects and advantages of these devices and methods are described below. However, it should be understood that the principles involved in these devices and methods can be employed in a variety of other contexts, and therefore the novel devices and method disclosed and claimed here should not be construed as being limited to the example embodiments described below.

Toric intraocular lenses (IOLs) generally include fiducial marks which indicate their angular orientation within an eye. Currently, to view the fiducial marks, a patient's eye is dilated and a light is shined into the eye by means of which a physician may view the fiducial marks directly, or, for example, the fiducial marks may be seen on an image captured by a camera.

As described above, it would be desirable to provide a single measurement instrument which is capable of making wavefront measurements, making OCT measurements, and determining the angular orientation of an implanted toric IOL in an eye. While it may be possible to simply add to an objective eye measurement instrument a separate illumination system to view the fiducial marks, this may add additional complexity and expense to the measurement instrument. So, there is a desire for other, perhaps more elegant, solutions.

Toward this end, the present inventors have determined that it would be desirable to provide pupil retro illumination using an optical path and optical componentry which is already present in the optical coherence tomographer of the instrument. A principal advantage of this solution is that it may reduce the cost and complexity of the pupil retro illumination subsystem.

One simple method is for the system to include a light source that is coupled into the eye using the same fiber launch optics that the OCT system uses. A different wavelength should be used for the pupil retroillumation so a wavelength splitting beam splitter (long pass or short pass) can be used to direct the light to the OCT or camera paths the most efficiently. For the OCT wavelength, the beam splitter should be highly reflective. For the pupil retroillumination wavelength the beamsplitter should be partially reflecting so the beam splitter both injects the beam into to the eye and allows transmission of light to the camera.

To provide spatial resolution of structures in the eye, the OCT launch optics produce a beam that is nearly collimated. Such a beam will often create a pupil retroillumination pattern that only partially fills the pupil and does not extend out to the fiducial marks on the IOL that we wish to view in order to determine the orientation of the IOL within the eye. The fraction of the pupil that fills in will be dependent on the refractive strength of the eye, with strong myopes and strong hyperopes having partially filled in light patterns. This effect is particularly pronounced if the system uses a small aperture in the camera beam path that limits the range of ray angles that can reach the camera. Small apertures of that kind are used in systems that use the camera to measure corneal topography. In that case, the aperture can be moved out of the beam path during the retroillumination image capture by means of a motorized actuator. A second, separate, solution is to move the OCT scan mirror in a pattern that causes the spot to move on the retina, and that causes the entire pupil to fill in with light over time even when the aperture is left in place. The motion of the scan pattern should be completed within the image capture time of a single frame of the camera. Typical camera integration times are around thirty milliseconds, and scanner rates are in the kilohertz so the required motions are easily achievable. A single general purpose scan pattern can meet the backfilling requirements for the range of myopes, emmetropes and hyperopes. It is possible to decrease the amount of light required to back fill the eye and/or shorten the required camera exposure time by adjusting the scan pattern to match a known refractive power of the eye. Such information could be provided by a refraction measuring device, such as a wavefront sensor, that is included in the same instrument.

FIG. 1A illustrates an example embodiment of an optical coherence interferometry (OCT) interferometer 1000A which provides pupil retro illumination via its sample arm.

In particular, OCT interferometer 1000A may be employed for swept-source OCT (SS-OCT) of an eye 101 under test, as is known in the art, including an eye 101 under test which may include an implanted intraocular lens (IOL), for example a toric IOL.

OCT interferometer 1000A includes a swept laser light source 1010, a variable optical attenuator (VOA) 1015, a first fiber splitter 1020, a reference path 1100, a sampling path 1200, a second fiber splitter 1030, and a detector 1050.

Reference path 1100 includes a first optical fiber 1110, a second optical fiber 1120, and a second VOA 1140. Reference path 1100 may further include a polarizer (not shown in FIG. 1A). Beneficially, reference path 1100 has a defined optical path length.

In some embodiments, first optical fiber 1110 and second optical fiber 1120 which are connected in series with each other may have different group velocity dispersion characteristics from each other, as described in greater detail in U.S. Provisional Patent Application 62/419,890, filed on 9 Nov. 2016, entitled "OPTICAL COHERENCE TOMOGRAPHY SYSTEMS AND METHODS WITH DISPERSION COMPENSATION," which is incorporated herein by reference.

Sampling path 1200 includes an optical fiber 1210, a polarizer 1215, a coupler 1217, a Z-scan device 1220, a scanner 1230, and one or more optical lenses 1240, and delivers an OCT probe beam 1214 into an eye 101 under test. Z-scan device 1220 may comprise a Z-telescope which may be controlled by a controller (not shown in FIG. 1) to focus OCT probe beam 1214 at a desired depth within eye 101. Scanner 1230 scans the probe beam in X and Y directions to span an X-Y OCT measurement space in eye 101. In some embodiments, scanner 1230 may comprise an X-Y scanner. In other embodiments, scanner 1230 may comprise a separate X-scanner and a separate Y-scanner.

Beneficially, detector 1050 may comprise a balanced photodiode detector.

In operation, the wavelengths for swept laser light source 1010 may be centered at wavelengths from 840 nm to 1310 nm in the near infrared spectrum. As a non-limiting example, OCT interferometer 1000A may be configured to employ a swept source having wavelengths of around 1060 nm with an 8 mm scan depth. The spatial disposition of the eye structures using optical coherence tomography should generally be measured while the patient is engaged with a patient interface, as described below. The OCT scan depth may be between 8 and 50 mm, and the scan depth may be greater than about 24 mm or even 30 mm to achieve a full scan depth for eye 101.

Sample path 1200 is configured to receive a first portion of the laser light from swept laser light source 1010 via first fiber splitter 1020, to direct the first portion of the laser light to eye 101 as a probe beam 1214, and to receive a returned portion of the probe beam from eye 101, returned by reflection and/or scattering and to direct the returned portion of probe beam 1214 to detector 1050 via second fiber splitter 1030.

Reference path 1100 is configured to receive a second portion of the laser light from swept laser light source 1010 via first fiber splitter 1020, and to pass the second portion of the laser signal therethrough to detector 1050 via second fiber splitter 1030.

Detector 1050 is configured to receive the returned portion of the probe beam from eye 101, returned by reflection and/or scattering, and to also receive the second portion of the laser light from swept laser light source 1010 which passed through reference path 1100, and in response thereto to output an OCT signal having optical peaks whose relative timing representing the depths of various reflection and scattering surfaces within eye 101. Beneficially, detector 1050 may comprise a balanced photodiode detector which generates and outputs an OCT signal based on an interference pattern between the returned portion of the probe beam from eye 101, returned by at least one reflection and scattering, and the second portion of the laser light from swept laser light source 1010 which passed through reference path 1100.

Further details about the operating principles of an OCT interferometer for SS-OCT are known and a description thereof will not be repeated here for brevity.

FIG. 1A also illustrates a pupil retro illumination light source (e.g., a laser) 1300 whose laser light output 1301 is provided to coupler 1217 and coupled thereby into sample path 1200 and thence onto the retina of eye 101 which, e.g., includes an implanted IOL. In the illustrated example, pupil retro illumination light source 1300 operates at 904 nm (near infrared spectrum), which is different than the wavelength of swept laser light source 1010 of the OCT interferometer, but it should be understood that other appropriate wavelengths may be employed.

In some embodiments, as described in greater detail below with respect to FIGS. 3A-3C, 4, 5A-5B and 6, an optical measurement instrument may include OCT interferometer 1000A, pupil retro illumination light source 1300, a wavefront aberrometer, a camera (i.e., an iris camera), and a processor which may process one or more images captured by the camera and/or data obtained by OCT interferometer 1000A and the wavefront aberrometer, as discussed below.

In operation, the laser light 1301 from pupil retro illumination light source 1300 is coupled through coupler 1217 to the retina of eye 101, passing through the implanted IOL in eye 101. Light is reflected back from the retina of eye and captured on a camera (i.e., an iris camera) not shown in FIG. 1A. Beneficially, as mentioned above, scanner 1230 may be controlled by a controller or processor (not shown in FIG. 1A) to scan laser light 1301 in a pattern that causes the spot which it produces on the retina of eye 101 to move, and that causes the entire pupil of eye 101 to fill in with light over the time frame of a single captured image. Again, the motion of the scan pattern should be completed within the image capture time of a single frame of the camera, One or more fiducials which are provided on the implanted IOL, and whose locations or positions change with the angular orientation of the IOL, may appear as shadows or dark spots on the captured image, and these shadows or dark spots may be detected in the captured image, for example, by a processor using a feature or pattern recognition software algorithm. The angular orientation of the IOL then can be ascertained or determined from the detected fiducials, for example by the processor mentioned above.

Optionally, the wavefront aberrometer may make measurements of eye 101 to ascertain the magnitude of astigmatism and the refractive cylinder axis of eye 101 with the IOL implanted.

Assuming that the cylinder power of the IOL is known, and if it is provided to the processor for example via a user interface of the optical measurement instrument, then the processor may ascertain or determine the angular orientation at which the IOL should have been disposed within the eye in order to produce optimal vision, using the measured magnitude of the astigmatism of the eye, the measured refractive cylinder axis of the eye, and the known cylinder power of the IOL.

Furthermore, OCT interferometer 1001A may make OCT measurements of eye 101 from which the position of the implanted IOL within eye 101 may be ascertained or determined.

Figure 1B:
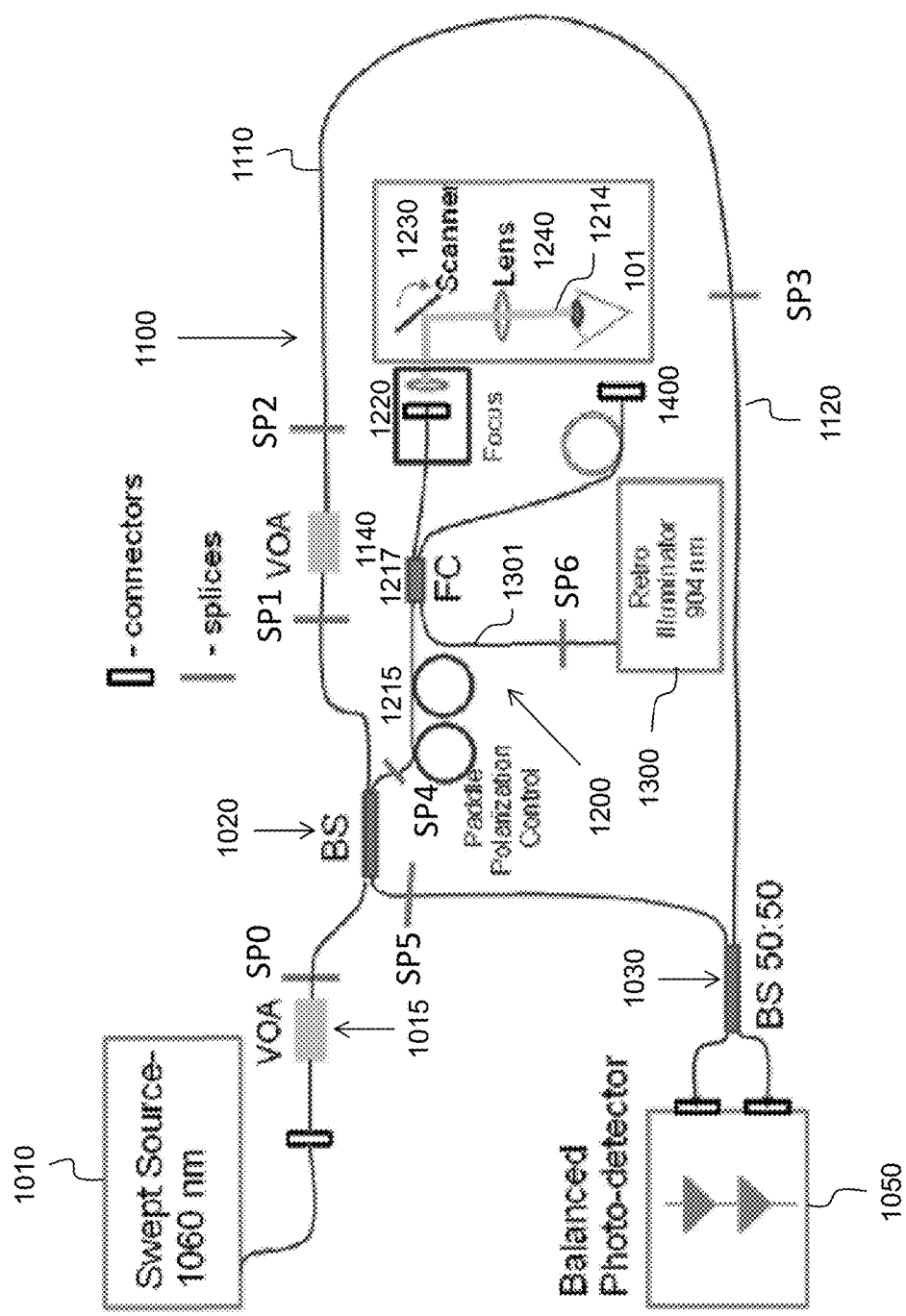
FIG. 1B illustrates another example embodiment of an OCT interferometer which provides pupil retro illumination via its sample arm.

FIG. 1B illustrates an example embodiment of an optical coherence interferometry (OCT) interferometer 1000B which provides pupil retro illumination via its sample arm.

OCT interferometer 1000B is very similar to OCT interferometer 1000A, and only the differences therebetween will be described. Here, the significant difference between OCT interferometer 1000A and OCT interferometer 1000B is that OCT interferometer 1000B includes a reference fiducial signal generator 1400 for the OCT measurement (not be confused with the fiducials which are provided on a toric IOL to determine its angular orientation).

Figure 2:
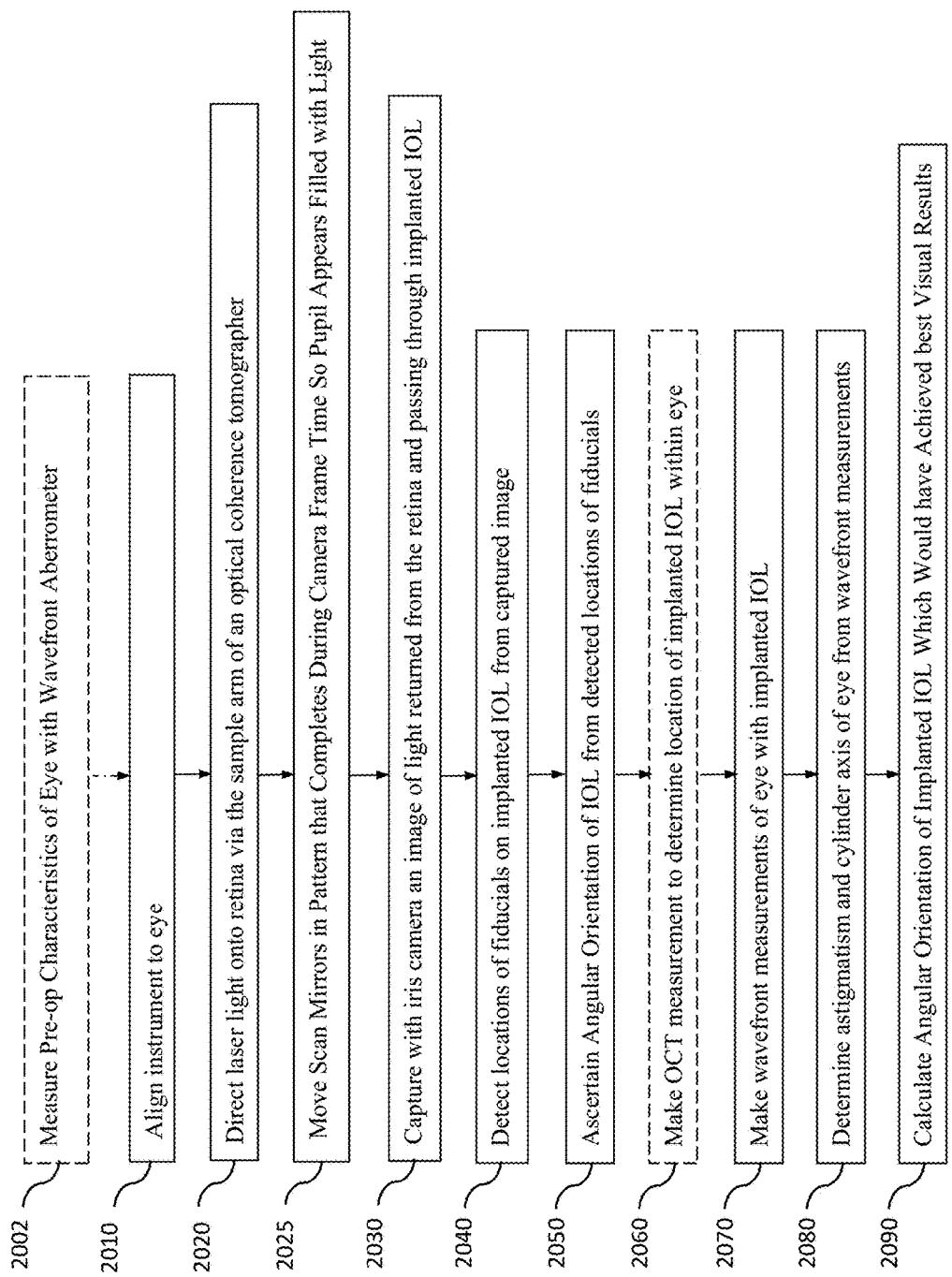
FIG. 2 is a flowchart of an example embodiment of a method of determining an angular orientation of an implanted intraocular lens in an eye using pupil retro illumination provided by the sample arm of an OCT interferometer.

FIG. 2 is a flowchart of an example embodiment of a method 2000 of measuring one or more characteristics of an eye with an optical measurement instrument which includes at least an OCT interferometer and a pupil retro illumination light source, such as OCT interferometer 1000A or 1000B and pupil retro illumination light source 1300.

An optional operation 2002 includes employing a wavefront aberrometer (e.g., a Shack-Hartmann wavefront aberrometer) of a measurement instrument to measure preoperation characteristics of an eye into which an IOL, and particularly a toric IOL, is to be implanted. Such characteristic may include the magnitude of any astigmatism of the eye, and the corresponding cylinder axis. Such pre-op data may be used after surgery to assess changes to the eye's visual performance as a result of surgery.

Subsequently, it is assumed that surgery is performed to implant an IOL, and specifically in this example a toric IOL, into the eye.

An operation 2010 includes, at some time after the IOL has been implanted in the eye, aligning the measurement instrument, including the OCT interferometer, to the eye to be measured.

An operation 2020 includes directing laser light from a pupil retro illumination light source onto the retina of the eye via the sample arm of an optical coherence tomographer, including passing the pupil retro illumination light through an implanted IOL in the eye.

An operation 2025 includes moving the scan mirrors in a pattern which completes within the time interval of a single frame of an iris camera, so that an image may be captured in the time period of one frame where the pupil appears to be filled with light. For example, where the iris camera captures 30 frames per second (fps), then the time period of one frame is about 33 milliseconds, and in this case the scan mirrors move in a pattern such that the light returning from the scanned areas of the retina fills the pupil over the time interval of 33 milliseconds.

An operation 2030 includes capturing with the iris camera an image of the pupil retro illumination light returned from the retina of the eye and passed back through the implanted IOL.

An operation 2040 includes detecting the locations of fiducials on the implanted IOL in the captured image. In some embodiments, the fiducials may be disposed at predefined angular locations at the periphery of the IOL. In that case, the locations of the fiducials in the captured image would change depending on the angular orientation of the implanted IOL in eye 10. In some embodiments, the fiducials may comprise dark spots disposed at predefined angular locations at the periphery of the IOL. In that case, in operation 2040, the locations of the fiducials in the captured image may be detected as the locations of dark spots in the captured image. In some embodiments, a processor may employ feature recognition or pattern recognition software algorithm to detect the locations of the locations of fiducials on the implanted IOL in the captured image.

An operation 2050 includes ascertaining the angular orientation of the implanted IOL from the detected locations of fiducials in the captured image. In particular, it is assumed that a processor has access to data identifying the actual locations of the fiducials on the implanted IOL, for example from data which may be supplied to the processor via a user interface of the optical measurement instrument. In that case, by comparing the locations of the fiducials in the captured image to the known locations of the fiducials which would change depending on the angular orientation of the implanted IOL in eye 101, the processor can easily determine the angular orientation of the IOL within the eye.

An operation 2060 includes performing an OCT measurement to determine the location of the implanted IOL within eye. In some embodiments, operation 2060 may be omitted.

An operation 2070 includes making wavefront measurements of eye 101 with the implanted IOL. In some embodiments, the wavefront measurements may be made using a Shack-Hartmann wavefront aberrometer which is included in the same measurement instrument as OCT interferometer 1000A or 1000B and pupil retro illumination light source 1300.

An operation 2080 includes determining the magnitude of the astigmatism of eye 101 and the cylinder axis of eye 101 from the wavefront measurements.

An operation 2090 includes calculating the angular orientation of the implanted IOL which would have achieved the best visual results for eye 101 after implantation.

The principles of OCT interferometers 1000A and 1000B, pupil retro illumination light source 1300, and method 2000, as described above, may be applied to an optical measurement instrument which includes additional functionality, such as the ability to measure corneal topography and/or to make wavefront aberrometry measurements for they eye. Embodiments of such an optical measurement instrument, and methods of operation thereof, will now be described.

As shown in FIGS. 3A-3C, an optical measurement system 1, according to many embodiments, is operable to provide for a plurality of measurements of the human eye, including wavefront aberrometry measurements, corneal topography measurements, and optical coherence tomography measurements to measure characteristics of the cornea, the lens capsule, the lens and the retina. Optical measurement system includes a main unit 2 which comprises a base 3 and includes many primary subsystems of many embodiments of optical measurement system 1. For example, externally visible subsystems include a touchscreen display control panel 7, a patient interface 4 and a joystick 8.

Patient interface 4 may include one or more structures configured to hold a patient's head in a stable, immobile and comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by optical measurement system 1.

In one embodiment patient interface 4 includes a chin support 6 and/or a forehead rest 5 configured to hold the head of the patient in a single, uniform position suitably aligned with respect to optical measurement system 1 throughout the diagnostic measurement. As shown in FIG. 3C, the optical measurement system 1 may be disposed so that the patient may be seated in a patient chair 9. Patient chair 9 can be configured to be adjusted and oriented in three axes (x, y, and z) so that the patent's head can be at a suitable height and lateral position for placement on the patient interface.

In many embodiments, optical measurement system 1 may include external communication connections. For example, optical measurement system 1 can include a network connection (e.g., an RJ45 network connection) for connecting optical measurement system 1 to a network. The network connection can be used to enable network printing of diagnostic reports, remote access to view patient diagnostic reports, and remote access to perform system diagnostics. Optical measurement system 1 can include a video output port (e.g., HDMI) that can be used to output video of diagnostic measurements performed by optical measurement system 1. The output video can be displayed on an external monitor for, for example, viewing by physicians or users. The output video can also be recorded for, for example, archival purposes. Optical measurement system 1 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed at a later time for any suitable purpose such as, for example, printing from an external computer in the case where the user without access to network based printing or for use during cataract surgery, including laser cataract surgery.

Figure 4:
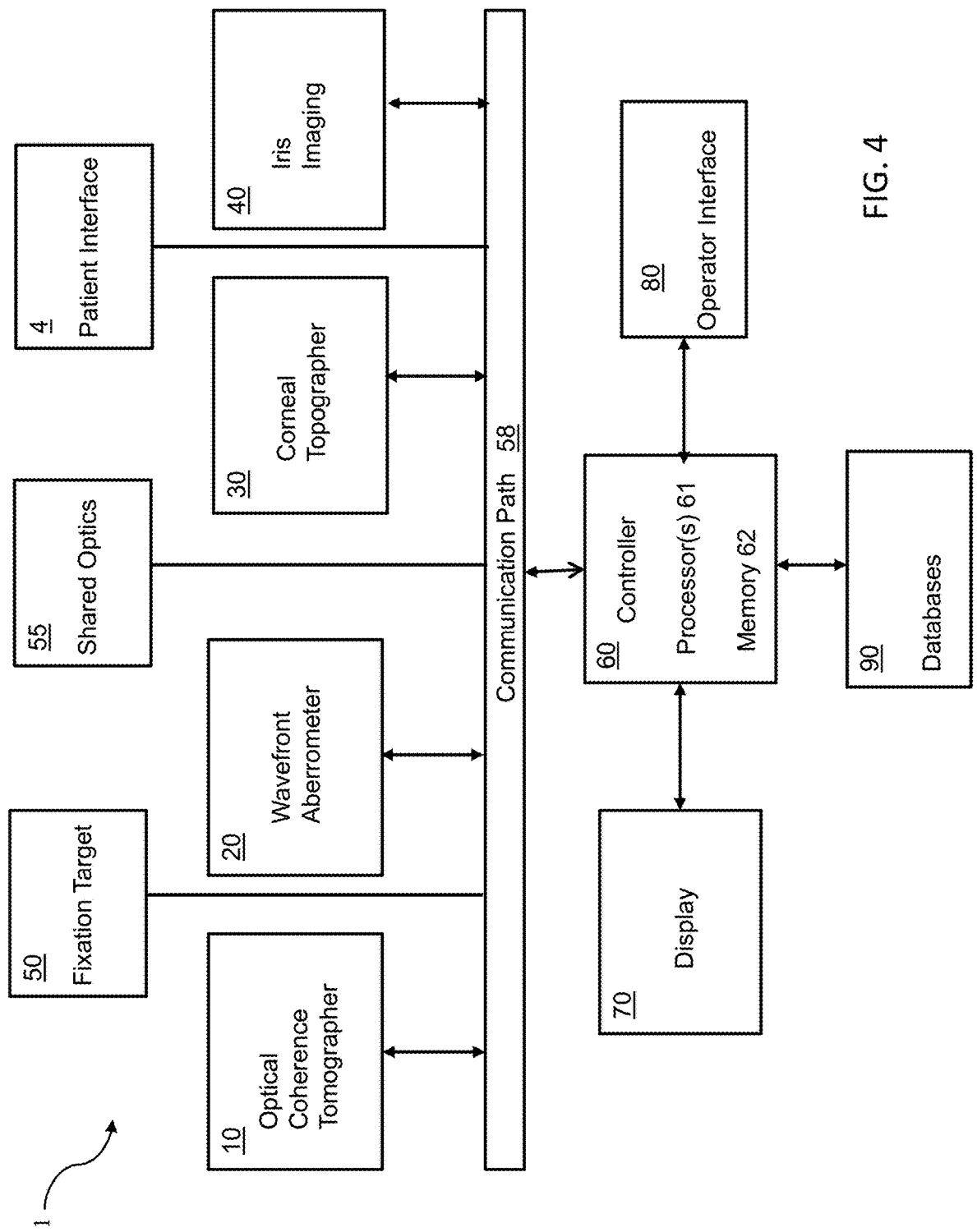
FIG. 4 is a block diagram of a system including an optical measurement instrument, and a position of an eye relative to the system according to one or more embodiments described herein which may be used by the optical measurement.

FIG. 4 is a block diagram of optical measurement system 1 according to one or more embodiments described herein. Optical measurement system 1 includes: an optical coherence tomography (OCT) subsystem 10, a wavefront aberrometer subsystem 20, and a corneal topographer subsystem 30 for measuring one or more characteristics of a subject's eye. Optical measurement system 1 may further include an iris imaging subsystem 40, a fixation target subsystem 50, a controller 60, including one or more processor(s) 61 and memory 62, a display 70 and an operator interface 80. Optical measurement system 1 further includes patient interface 4 for a subject to present his or her eye for measurement by optical measurement system 1.

Optical coherence tomography subsystem 10 is configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by controller 60 for a number of purposes, including, in some embodiment to program and control a subsequent laser-assisted surgical procedure. The spatial disposition of the structures of interest and/or of suitable matching geometric modeling can also be used to determine a wide variety of parameters. Beneficially, optical coherence tomography subsystem 10 may employ swept source optical coherence tomography (SS-OCT) as described above. Beneficially, optical coherence tomography subsystem 10 may comprise OCT interferometer 1000A or 1000B.

Wavefront aberrometer subsystem 20 is configured to measure ocular aberrations, which may include low and high order aberrations, by measuring the wavefront emerging from the eye by, for example a Shack Hartman sensor.

Corneal topographer subsystem 30 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Shack-Hartmann measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4.

Iris imaging subsystem 40 may include an iris camera and a pupil retro illumination light source such as pupil retro illumination light source 1301 which directs pupil retro illumination light to the retina of the eye via the sample path of optical coherence tomography subsystem 10. In some embodiments, the iris camera may comprise a detector array, such as a charge-coupled device (CCD) or CMOS detector array. In some embodiments, the iris camera may be shared with one or more other subsystems of optical measurement system 1, such as corneal topographer subsystem 30.

Fixation target subsystem 50 is configured to control the patient's accommodation, because it is often desired to measure the refraction and wavefront aberrations when an eye under measurement is focused at its far point Images captured by corneal topographer subsystem 10, wavefront aberrometer 20, optical coherence tomographer subsystem 30 and/or iris imaging subsystem 40 may be displayed with a display of operator interface 80 or display 70 of optical measurement system 1, respectively. Operator interface 80 may also be used to modify, distort, or transform any of the displayed images.

Shared optics 55 provide a common propagation path that is disposed between patient interface 4 and each of optical coherence tomography (OCT) subsystem 10, wavefront aberrometer subsystem 20, corneal topographer subsystem 30, and in some embodiments, iris imaging subsystem 40, and fixation target subsystem 50. In many embodiments, shared optics 55 may comprise a number of optical elements, including mirrors, lenses and beam combiners to receive the emission from the respective subsystem to the patient's eye and, in some cases, to redirect the emission from a patient's eye along the common propagation path to an appropriate director.

Controller 60 controls the operation of optical measurement system 1 and can receive input from any of optical coherence tomographer (OCT) subsystem 10, wavefront aberrometer subsystem 20, corneal topographer subsystem 30 for measuring one or more characteristics of a subject's eye, iris imaging subsystem 40, fixation target subsystem 50, display 70 and operator interface 80 via communication paths 58. Controller 60 can include any suitable components, such as one or more processor, one or more field-programmable gate array (FPGA), and one or more memory storage devices. In many embodiments, controller 60 controls display 70 to provide for user control over the laser eye surgery procedure for pre-cataract procedure planning according to user specified treatment parameters as well as to provide user control over the laser eye surgery procedure. Communication paths 58 can be implemented in any suitable configuration, including any suitable shared or dedicated communication paths between controller 60 and the respective system components.

Operator interface 80 can include any suitable user input device suitable to provide user input to controller 60. For example, user interface devices 80 can include devices such as joystick 8, a keyboard, or a touchscreen display.

Figure 5A:
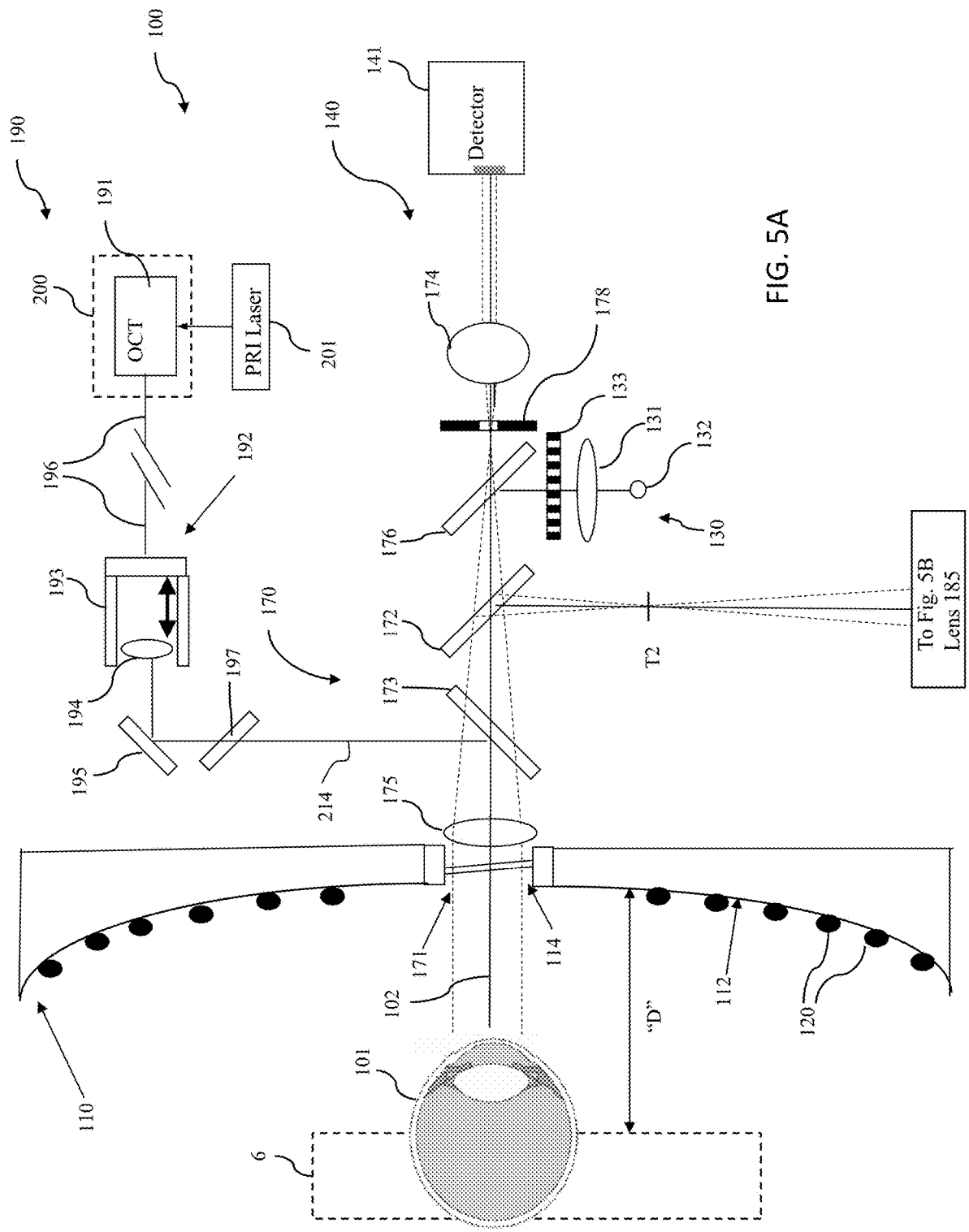
FIGS. 5A and 5B illustrate together an assembly illustrating a suitable configuration and integration of an optical coherence tomographer subsystem, a wavefront aberrometer subsystem a corneal topographer subsystem, an iris imaging subsystem, a fixation target subsystem according to a non-limiting embodiment of the present invention.
Figure 5B:
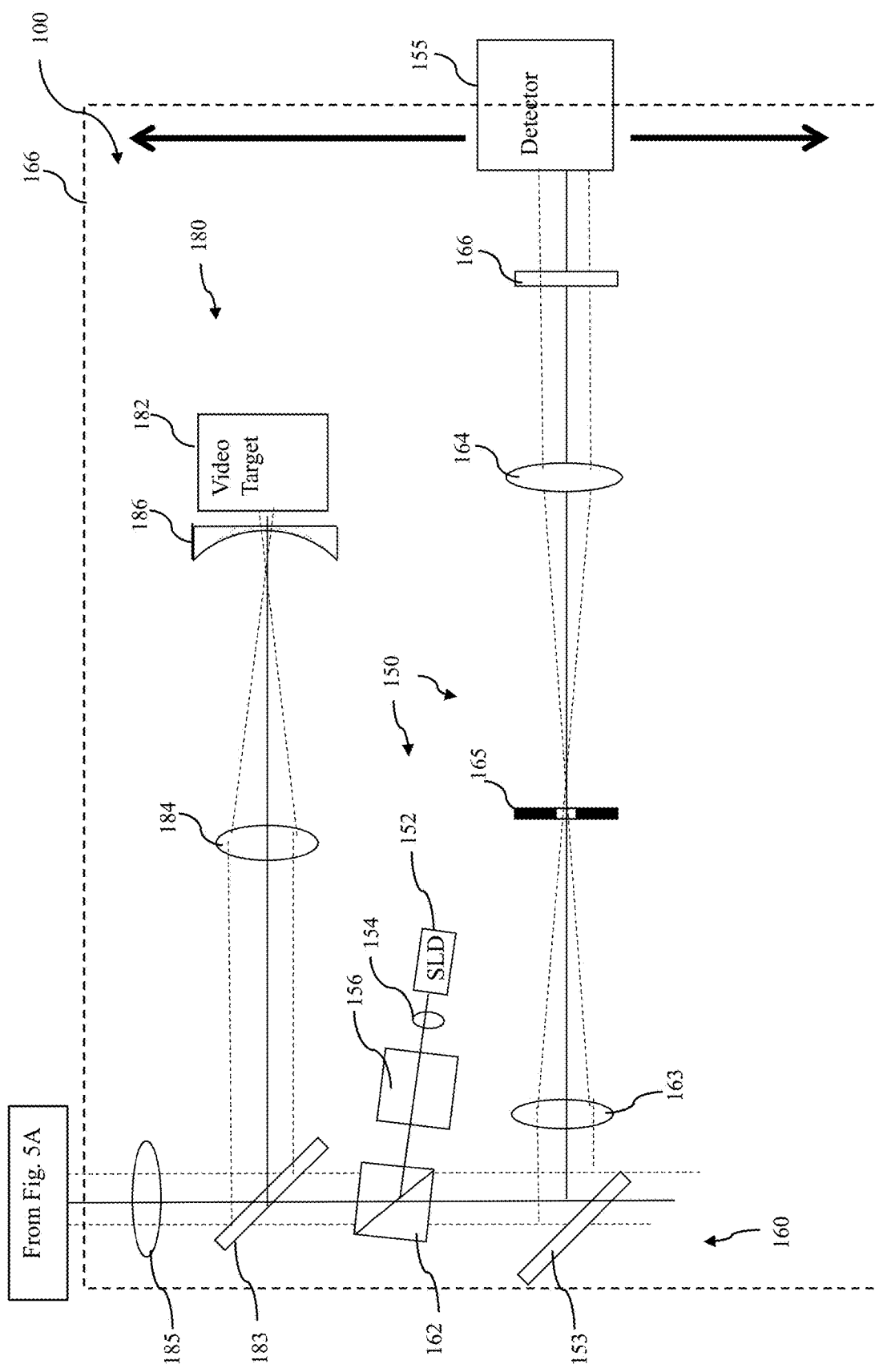

FIGS. 5A and 5B are simplified block diagrams illustrating an assembly 100 according to some embodiments which may be included in optical measurement system 1. Assembly 100 is a non-limiting example of suitable configurations and integration of an optical coherence tomography (OCT) subsystem 190, a wavefront aberrometer subsystem 150, a corneal topographer subsystem 140 for measuring one or more characteristics of a subject's eye, an imaging subsystem including a pupil retro illumination light source 201, a fixation target subsystem 180 and shared optics.

The shared optics generally comprise one or more components of a first optical system 170 disposed along a central axis 102 passing through the opening or aperture 114 of the structure 110. First optical system 170 directs light from the various light sources along the central axis 102 towards an eye 101 and establishes a shared or common optical path along which the light from the various light sources travel to eye 101. In one embodiment, optical system 170 comprises a quarter wave plate 171, a first beamsplitter 172, a second beamsplitter 173, an optical element (e.g., a lens) 174, a second lens 175, a third beamsplitter 176, and a structure including an aperture 178. Additional optical systems may be used in assembly 100 to direct light beams from one or more light sources to the first optical system 170. For example, a second optical system 160 directs light to the first optical system 170 from wavefront aberrometer subsystem 150 and comprises mirror 153, beam splitter 183 and lens 185.

Other configurations of assembly 100 may be possible and may be apparent to a person of skill in the art.

Corneal topographer subsystem 140 comprises a structure 110 having a principal surface 112 with an opening or aperture 114 therein; a plurality of first (or peripheral) light sources 120 provided on the principal surface 112 of structure 110; a Helmholz light source 130; and a detector, photodetector, or detector array 141, which may also serve as an iris camera.

In one embodiment, structure 110 has the shape of an elongated oval or "zeppelin" with openings or apertures at either end thereof. An example of such a structure is disclosed in Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 101, as illustrated in FIG. 5A.

In one embodiment where principal surface 112 is concave, principal surface 112 has the shape of a conical frustum. Alternatively, principal surface 112 may have a shape of hemisphere or some other portion of a sphere, with an opening or aperture therein. Also alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 1001 without being obstructed by the subject's nose. Of course, a variety of other configurations and shapes for principal surface 112 are possible.

In the embodiment of FIG. 5A, the plurality of first light sources 120 are provided on the principal surface 112 of structure 110 so as to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 101. Other arrangements are possible.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 5A).

In operation, a ray (solid line) from one of the first light sources 120 is reflected by the cornea and passes through optical system 170 (including aperture 178) to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered so as to not pass through the optical system 170. In similar fashion, light from the other first light sources 120 are imaged onto detector array 141 such that each one of first light sources 120 is imaged or mapped to a location on detector array 141 that may be correlated to a particular reflection location on the cornea of eye 101 and/or the shape of the cornea. Thus, detector array 141 detects the light spots projected thereon and provides corresponding output signals to a processor of controller 60 (FIG. 4). The processor determines the locations and/or shape of the light spots on detector array 141, and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 60 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 101. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, lamps of second light sources 132 are located off the central optical axis 102 of assembly 100, and light from second light sources 132 is directed toward optical element 171 by third beamsplitter 176.

The operation of the corneal topographer portion of system 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 141 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141, and compares these locations and/or shapes to those expected based for a standard or model cornea, thereby allowing the processor to determine the corneal topography of eye 101. Accordingly, the topography of the entire corneal surface can be characterized by system 100 without a "hole" or missing data from the central corneal region.

Wavefront aberrometer subsystem 150 of assembly 100 comprises a third light source 152 providing a probe beam and a wavefront sensor 155. Wavefront aberrometer subsystem 150 preferably further comprises a collimating lens 154, a polarizing beamsplitter 156, an adjustable telescope comprising a first optical element, lens 163 and a second optical element, lens 164, a movable stage or platform 166, and a dynamic-range limiting aperture 165 for limiting a dynamic range of light provided to wavefront sensor 155 so as to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 may be an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Beneficially, wavefront sensor 155 may be a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows assembly 100 to provide a probe beam into eye 101 to characterize its total ocular aberrations. Accordingly, third light source 152 supplies a probe beam through a light source polarizing beam splitter 156 and polarizing beam splitter 162 to first beamsplitter 172 of optical system 170. First beamsplitter 172 directs the probe beam through aperture 114 to eye 101. Preferably, light from the probe beam is scattered from the retina of eye 100, and at least a portion of the scattered light passes back through aperture 114 to first beamsplitter 172. First beamsplitter 172 directs the back scattered light back through beam splitter 172 to polarizing beamsplitter 162, mirror 153 to wavefront sensor 155.

Wavefront sensor 155 outputs signals to a processor of controller 60 which uses the signals to determine ocular aberrations of eye 101. Preferably, the processor is able to better characterize eye 101 by considering the corneal topography of eye 101 measured by corneal topography subsystem 140, which may also be determined by the processor based on outputs of detector array 141, as explained above.

In operation of wavefront aberrometer subsystem 150, light from light source 152 is collimated by lens 154. The light passes through light source polarizing beam splitter 156. The light entering light source polarizing beam splitter 156 is partially polarized. Light source polarizing beam splitter 156 reflects light having a first, S, polarization, and transmits light having a second, P, polarization so the exiting light is 100% linearly polarized. In this case, S and P refer to polarization directions relative to the hypotenuse in light source polarizing beam splitter 156.

Light from light source polarizing beam splitter 156 enters polarizing beamsplitter 162. The hypotenuse of polarizing beamsplitter 162 is rotated 90 degrees relative to the hypotenuse of light source polarizing beamsplitter 156 so the light is now S polarized relative the hypotenuse of polarizing beamsplitter 162 and therefore the light reflects upwards. The light from polarizing beamsplitter 162 travels upward and passes through toward beam splitter 172, retaining its S polarization, and then travels through quarter wave plate 171. Quarter wave plate 171 converts the light to circular polarization. The light then travels through aperture 114 in principal surface 112 of structure 110 to eye 101. Preferably, the beam diameter on the cornea is between 1 and 2 mm. Then the light travels through the cornea and focuses onto the retina of eye 101.

The focused spot of light becomes a light source that is used to characterize eye 101 with wavefront sensor 155. Light from the probe beam that impinges on the retina of eye 101 scatters in various directions. Some of the light reflects back as a semi-collimated beam back towards assembly 100. Upon scattering, about 90% of the light retains its polarization. So the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe beam received from third light source 150 having the S polarization. This P polarized light then reflects off of first beamsplitter 172, and then reaches polarizing beamsplitter 162. Since the light is now P polarized relative the hypotenuse of polarizing beamsplitter 162, the beam is transmitted and then continues onto mirror 153. After being reflected by mirror 153, light is sent to an adjustable telescope comprising a first optical element 164 and a second optical element (e.g., lens) 163 and a movable stage or platform 166. The beam is also directed through a dynamic-range limiting aperture 165 for limiting a dynamic range of light provided to wavefront sensor 155 so as to preclude data ambiguity.

When wavefront sensor 155 is a Shack-Hartmann sensor, the light is collected by the lenslet array in wavefront sensor 155 and an image of spots appears on the detector array (e.g., CCD) in wavefront sensor 155. This image is then provided to a processor of controller 60 and analyzed to compute the refraction and aberrations of eye 101.

OCT subsystem 190 of assembly 100 may comprise an OCT assembly 191, and a third optical path 192 which directs the OCT beam of the OCT light source to the first optical path 170. The third optical path 192 may comprise a fiber optic line 196, for conducting the OCT beam from the OCT light source of OCT assembly 191, a Z-scan device 193 operable to alter the focus of the beam in the Z-direction (i.e., along the direction of propagation of the OCT beam)

under control of the controller, and X-scan device 195, and a Y-scan device 197 operable to translate the OCT beam in the X and Y directions (i.e., perpendicular to the direction of propagation of the of the OCT beam), respectively, under control of controller 60. The OCT light source and reference arm may be incorporated into assembly 100 of optical measurement system 1 shown in FIG. 5A. Alternatively, OCT assembly 191 may be housed in a second unit or housing 200 and the OCT beam from the OCT source may be directed from second unit 200 to the main unit by optical pathway 192.

Beneficially, the OCT systems and methods employed in optical measurement system 1 and assembly 100 may employ swept source optical coherence tomography (SS-OCT) as described above. Beneficially, optical measurement system 1, assembly 100 and OCT subsystem may each comprise OCT interferometer 1000A or 1000B.

As explained above, in SS-OCT, a rapid-scanning laser source is employed. By rapidly sweeping the source wavelength over a broad wavelength range, and collecting all the scattering and reflection information at each wavelength and at each position, the collected spectral data may be inverse Fourier transformed to recover the spatial depth-dependent information for the object under test (e.g., eye 101).

Pupil retro illumination light may be coupled from pupil retro illumination light source 201 into the sample path of OCT assembly 191, as described above with respect to FIGS. 1A and 1B, and directed along optical axis 102 by beam splitter 173 into the retina of eye 101. A portion of this light returns from the retina to image the IOL, including any fiducial marks on the IOL, onto detector 141 which here functions as an iris camea. If the IOL is imperfectly placed, detector 141 may be used to determine IOL edges are decentered. Also, images from detector 141 using the pupil retro illumination light returned from the retina may reveal folds, for instance, an unfolded edge if the IOL did not unfold properly when it was implanted.

Figure 6:
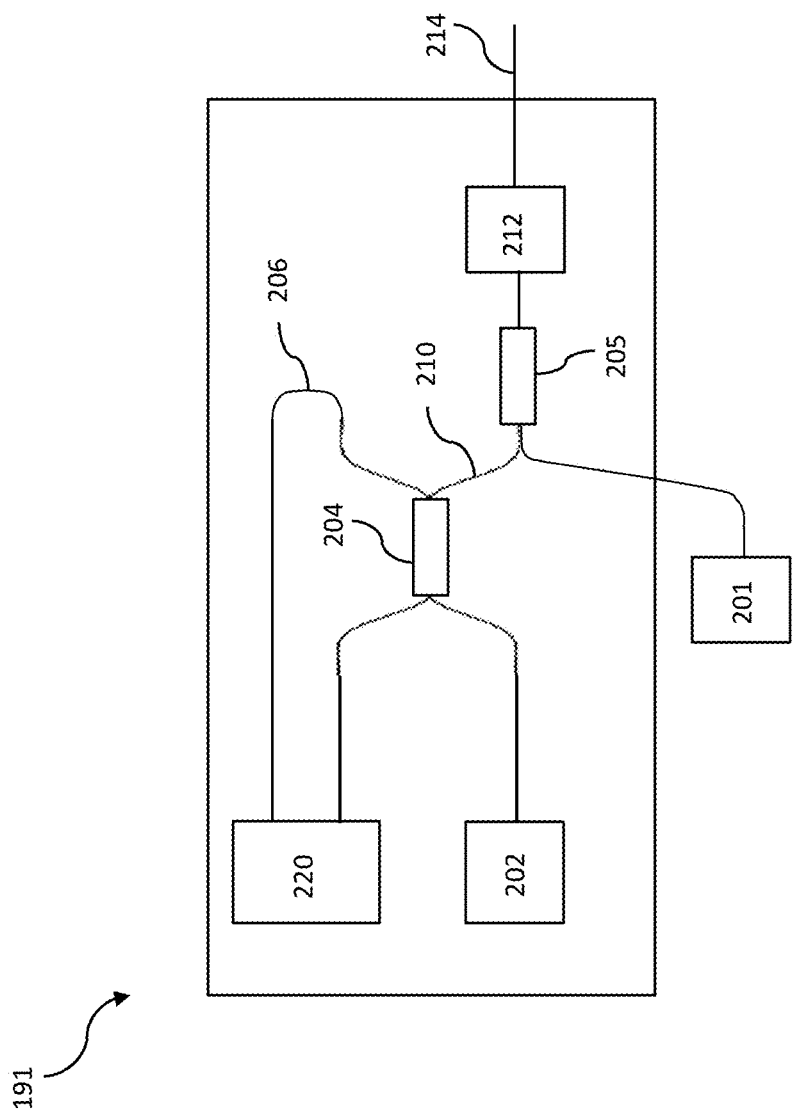
FIG. 6 is a block diagram of an OCT assembly according to one or more embodiments of the present invention.

As shown in FIG. 6, OCT assembly 191 of OCT subsystem 190 includes a swept light source 202 that is split by a coupler 204 into a reference path 206 and a sample path 210. Sample path 210 of OCT assembly 191 has an output connector 212 that serves as an interface to the rest of optical measurement system 1 for coupling the OCT probe beam of sample path 210 toward eye 101. The signal from reference path 206 and the returned reference signal from sample path 210 are then directed by coupler 204 to a detection device 220. In FIG. 6, a swept source technique may be used with a laser wavelength of 1060 nm swept over a range of 8-50 mm depth.

As also shown in FIG. 6, pupil retro illumination light may be coupled from pupil retro illumination light source 201 into the sample path of OCT assembly 191 via coupler 105 and thence along axis 102 to the retina of eye 101 (see FIG. 5A).

Figure 7:
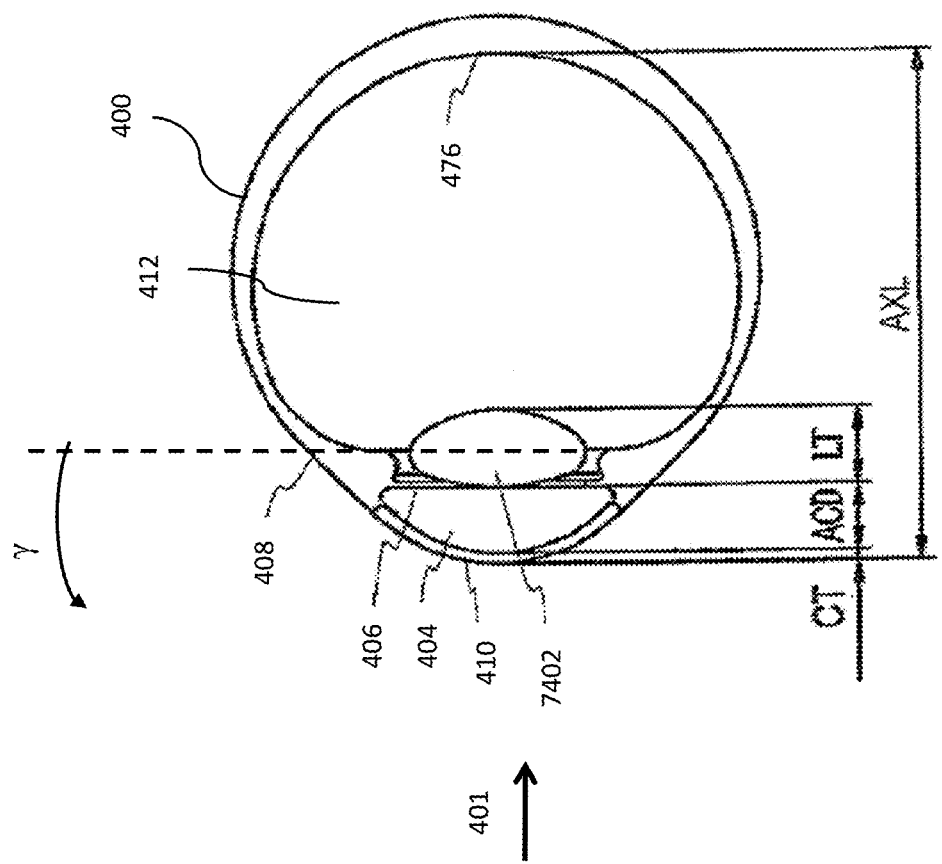
FIG. 7 is a schematic drawing of a human eye.

FIG. 7 is a schematic drawing of a human eye 400 having an IOL (e.g., a toric IOL 7402) implanted therein. In some embodiments, a light beam 401 from a light source enters the eye from the left of FIG. 7, refracts into the cornea 410, passes through the anterior chamber 404, the iris 406 through the pupil, and reaches implanted IOL 7402. After refracting into IOL 7402, light passes through the vitreous chamber 412, and strikes the retina 476, which detects the light and converts it to an electric signal transmitted through the optic nerve to the brain (not shown). The vitreous chamber 412 contains the vitreous humor, a clear liquid disposed between the lens 402 and retina 476. As indicated in FIG. 7, cornea 410 has a corneal thickness (CT), here considered as the distance between the anterior and posterior surfaces of the cornea. Anterior chamber 404 has anterior chamber depth (ACD), which is the distance between the anterior surface of the cornea and the anterior surface of the lens. Lens 402 has lens thickness (LT) which is the distance between the anterior and posterior surfaces of the lens. The eye has an axial length (AXL) which is the distance between the anterior surface of the cornea and the retina 476. FIG. 7 also illustrates that, in many subjects the lens, including the lens capsule, may be tilted at one or more angles relative to the optical axis, including an angle γ relative to the optical axis of the eye.

The optical system may also be arranged so that the movement pattern of the scan mirrors provides a lateral motion across the retina so that the shape of the retina may be determined. It is of particular interest to measure the shape and location of the depressed region of the retina named the foveal pit. When the patient is looking directly into the instrument, with their line of sight aligned to the fixation target, the foveal pit will be in center of the OCT lateral scan. This information is beneficial in that it informs the instrument operator if the patient was looking directly at the target when the measurement was made. Retinal scans are also useful in detecting disease conditions. In some cases there may be an absence of a foveal pit that also is considered an indication of a corneal abnormality.

The average axial length of the adult human eye is about 24 mm. Since the full range imaging depth of the OCT measurements are only about 5 mm to 8 mm, then OCT scanning may provide for OCT scans at different depths of the eye that can be combined together to form a combined OCT image of the eye. The OCT measurements may include OCT imaging at various depths of the patient's eye for imaging: (1) at least a portion of the retina, (2) at least a portion of the anterior portion of the eye, including at least a portion of the cornea (anterior and posterior), iris, and IOL 7402 (anterior and posterior), and (3) performing axial eye length measurements. From these measurements, the depth position or location of IOL 7402 may be ascertained.

FIGS. 8A-8C illustrate various aspects of OCT subsystem 190. FIG. 8A illustrates a preferred scanning region for OCT subsystem 190 according to many embodiments. The scanning region may be defined from starting point 301 to ending point 302 at the anterior portion of the eye extending in a direction transverse the direction of propagation of the OCT beam and also extending in a direction parallel to an axis defining the axial length of the eye to the posterior portion 304 of the eye. The lateral scanning region should generally be sufficiently large in the lateral direction to permit imaging of the central portion of the cornea, at least a portion of the iris, at least a portion of the lens and at least of the retina. It should be noted that a region 303 between the posterior portion of the lens and the surface of the retina may optionally not be scanned by OCT subsystem 190 because the portion 330 does not contain anatomical structure for 3D analysis.

FIG. 8B shows a representative graph of an intensity of an OCT signal of OCT subsystem 190 according to many embodiments as a function of depth along the axis defining the axial length of the eye. The graph generally exhibits approximately four peaks having a complex structure: (1) a peak 310 having a doublet-like structure and generally corresponding to a location of the cornea; (2) a peak 320 having a doublet-like structure and generally corresponding to a location of an anterior surface of the lens; (3) a peak 330 having a complex structure generally corresponding to a location of a posterior surface of the lens; and (4) a peak 340 generally corresponding to a location of a retina. A distance between peak 310 and peak 340 can be used to calculate the axial length (AL) of the eye. An OCT scan by OCT subsystem 190, including both an A-scan and B-scan, may be conducted for at least one location in the anterior portion of the eye (e.g., a location of a cornea, a location of an anterior surface of a lens and/or a location of a posterior surface of the lens) and at least one location in the posterior portion of the eye (e.g., at a location of a retina). In some embodiments, an OCT scan by OCT subsystem 190, including both an A-Scan and a B-scan is performed at a location corresponding to each of a location of the cornea, a location of an anterior surface of the lens, a location of a posterior surface of the lens, and a location corresponding to a retina.

It should be noted that because OCT subsystem 190 provides for the detection of various structures of the eye, including a location of the cornea, OCT subsystem 190 may be used as a ranging system to precisely align the patient in relation to optical measurement system 1. The use of OCT in a ranging system can significantly improve accuracy of corneal topography measurements, including keratometry measurements, which are sensitive to misalignment of the corneal structures.

FIG. 8C shows a cross-section of an eye obtained by an optical measurement system using an OCT subsystem such as OCT subsystem 190, which may employ an OCT interferometer such as OCT interferometer 1000A or 1000B.

Figure 9:
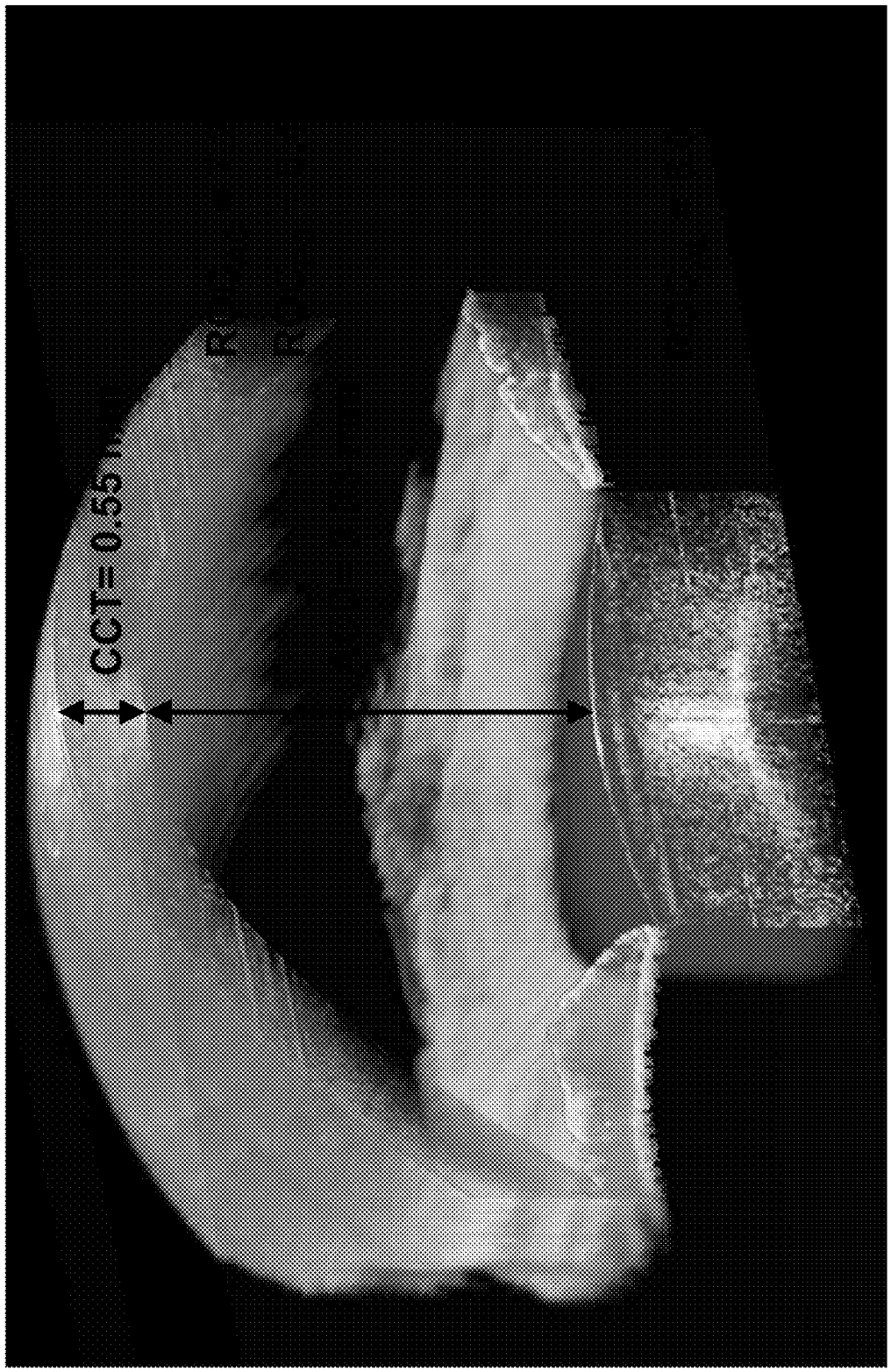
FIG. 9 is a 3-dimensional representation of an anterior portion of an eye obtained using the optical measurement system according to many embodiments.

FIG. 9 shows a 3 dimensional view of an eye obtained by an optical measurement system 1 using an OCT subsystem such as OCT subsystem 190. FIG. 9 evidences that the OCT subsystem is operable to obtain biometry measurements, including the central corneal thickness (CCT), the anterior chamber depth (ACD), the radius of curvature of the anterior cornea ($ROC_{AC}$), the radius of curvature of the Posterior cornea ($ROC_{PC}$) and the Radius of curvature of the axial length ($ROC_{AL}$).

OCT subsystem 190 may provide sufficiently resolved structural information to a structural assessment that may provide a user with an indication of suitability of a particular patient for a laser cataract procedure. In one embodiment, an OCT scan performed by OCT subsystem 190 at or near the retina (i.e., a retina scan) is sufficiently resolved to identify the foveal pit location and depth, wherein a lack of depression indicates an unhealthy retina.

In another embodiment, optical measurement system 1 provides one or more measurements sufficient to provide an assessment of the tear film of a patient. In one embodiment, the tear film assessment comprises a comparison of a wavefront aberrometry map and a corneal topography map or OCT map of the patient's eye, by, for instance, subtracting the corneal topography map from the wavefront aberrometry map, to obtain a difference map. A determination of whether the tear film is broken (if not smooth); an assessment of the tear film, including tear film breakup, can be obtained by reviewing the shape of spots on the topographer. For instance, a finding or indication that the tear film is disrupted, or broken, may be based upon the shape of a spot in that, if the spots are not round, and have, for instance, an oblong or broken up shape, it indicates that tear film is disrupted. The existence of such a disrupted tear film may indicate that K value, and other ocular measurements may not be reliable In operation, as shown in FIG. 5A, after exiting connector 212, an OCT probe beam 214 may be collimated, for example using a collimating optical fiber 196. Following collimating fiber 196 OCT probe beam 214 is directed to Z-scan device 193 operable to change the focal point of OCT probe beam 214 in the Z-direction, and X- and Y-scan devices 195 and 197, which are operable to scan the OCT beam in X and Y-directions perpendicular to the Z-direction.

Following the collimating optical fiber 196, OCT probe beam 214 continues through a Z-scan device 193. Z-scan device 193 may comprise a Z-telescope 194 which is operable to scan focus position of OCT probe beam 214 in the patient's eye 101 along the Z axis. For example, Z-telescope 194 may include a Galilean telescope with two lens groups (each lens group includes one or more lenses). One of the lens groups moves along the Z axis about the collimation position of Z-scan device 193. In this way, the focus position in the patient's eye 101 moves along the Z axis. In general, there is a relationship between the motion of lens group and the motion of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. Z-telescope 194 functions as a Z-scan device for changing the focus point of OCT probe beam 214 in patient's eye 101. Z-scan telescope 194 can be controlled automatically and dynamically by controller 60 and selected to be independent or to interplay with X and Y scan devices 195 and 197.

After passing through the z-scan device, the OCT probe beam 214 is incident upon an X-scan device 195, which is operable to scan the OCT probe beam 214 in the X direction, which is dominantly transverse to the Z axis and transverse to the direction of propagation of OCT probe beam 214. X-scan device 195 is controlled by controller 60, and can include suitable components, such as a lens coupled to a MEMS device, a motor, galvanometer, or any other well-known optic moving device. The relationship of the motion of OCT probe beam 214 as a function of the motion of the actuator of X-scan device 195 does not have to be fixed or linear. Modeling or calibrated measurement of the relationship or a combination of both can be determined and used to direct the location of OCT probe beam 214.

After being directed by the X-scan device 195, OCT probe beam 214 is incident upon a Y scan device 197, which is operable to scan OCT probe beam 214 in the Y direction, which is dominantly transverse to the X and Z axes. Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator of Y-scan device 197 does not have to be fixed or linear. Modeling or calibrated measurement of the relationship or a combination of both can be determined and used to direct the location of OCT probe beam 214. Alternatively, the functionality of X-Scan device 195 and Y-Scan device 197 can be provided by an XY-scan device configured to scan OCT probe beam 214 in two dimensions transverse to the Z axis and the propagation direction of OCT probe beam 214. The X-scan and Y scan devices 195, 197 change the resulting direction of OCT probe beam 214, causing lateral displacements of OCT probe beam 214 located in the patient's eye 101.

OCT probe beam 214 is then directed to beam splitter 173 through lens 175 through quarter wave plate 171 and aperture 114 and to the patient eye 101. Reflections and scattering off of structures within the eye provide return beams that retrace back through the patient interface quarter wave plate 171, lens 175, beam splitter 173, Y-scan device 197, X-scan device 195, Z-scan device 193, optical fiber 196 and beam combiner 204 (FIG. 6), and back into the OCT detection device 220. The returning back reflections of the sample arm 201 are combined with the returning reference portion 206 and directed into the detector portion of the OCT detection device 220, which generates OCT signals in response to the combined returning beams. The generated OCT signals that are in turn interpreted by controller 60 to determine the spatial disposition of the structures of interest in patient's eye 101. The generated OCT signals can also be interpreted by the controller to determine the spatial disposition of the structures of interest in the patient's eye 101. The generated OCT signals can also be interpreted by the control electronics to align the position and orientation of the patient eye within the patient interface.

Optical measurement systems disclosed herein may comprise an iris imaging subsystem 40. Iris imaging subsystem 40 generally may comprise an infrared light source, for example an infrared light source 152, and detector 141. In operation light from light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in XY and Z directions to align the patient according to the image detector array 141. In some embodiments of the iris imaging subsystem, eye 101 may be illuminated with infrared light from light source 152. In this way, the wavefront obtained by wavefront sensor 155 will be registered to the image from detector array 141.

The image that the operator sees is the iris of eye 100. The cornea generally magnifies and slightly displaces the image from the physical location of the iris. So the alignment that is done is actually to the entrance pupil of the eye. This is generally the desired condition for wavefront sensing and iris registration.

Iris images obtained by the iris imaging subsystem may be used for registering and/or fusing the multiple data sets obtained by the various subsystems of optical measurement system 1 by methods described, for instance, in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, both patient movement between measurements (and/or during a measurement sequence) can be identified, as well as changes in the eye itself (including those induced by the measurement, such as changes in the size of the pupil, changes in pupil location, etc.).

In many embodiments, optical measurement system 1 includes a target fixation subsystem 50 (FIG. 4), and assembly 100 shown in FIGS. 5A and 5B includes fixation target subsystem 180 which includes a fixation target 182 for the patient to view. Fixation target subsystem 180 is used to control the patient's accommodation, because it is often desired to measure the refraction and wavefront aberrations when eye 100 is focused at its far point (e.g., because LASIK treatments are primarily based on this). In the target fixation subsystem, a projection of a target, for instance a cross-hair pattern is projected onto the eye of the patient, the cross hair pattern being formed by a backlit LED and a film.

In operation, light originates from the light source 152 or, alternatively, from video target backlight 182 and lens 186. Lens 185 collects the light and forms an aerial image T2. This aerial image is the one that the patient views. The patient focus is maintained on aerial image 182 during measurement so as to maintain the eye in a fixed focal position.

The operating sequence the optical measurement system and methods of the present is not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In some embodiments, the operating sequence includes each of a wavefront aberrometry measurement, a corneal topography measurement and an OCT scan, wherein the OCT scan measures at least the locations of the retina, the cornea and one of an anterior portion or posterior of the patient's lens (e.g., an implanted IOL). An iris image may be taken simultaneously with or sequentially with each of the measurements taken with wavefront aberrometry subsystem, the corneal topography subsystem and the OCT subsystem, including an iris image taken simultaneously with or sequentially with the location of each OCT scan. This may result in improved accuracy in the 3-dimensional modeling of the patient's eye by permitting the various data sets to be fused and merged into a 3-dimensional model.

Optical measurement system 1 and the optical measurements obtained therewith may be used pre-operatively, i.e. before implanting an IOL (e.g., a toric IOL), for, e.g., eye biometry and other measurements, diagnostics and surgical planning. Surgical planning may include one or more predictive models. In the one or more predictive models, one or more characteristics of the postoperative condition of the patient's eye or vision is modeled based on one or more selected from the group consisting of pre-operative measurements obtained from the optical measurement system 1, a contemplated surgical intervention, and on or more algorithms or models stored in the memory of the optical measurement system 1 and executed by the processor. The contemplated surgical intervention may include the selection of an IOL for placement, the selection of an IOL characteristic, the nature or type of incision to be used during surgery (e.g., relaxation incision), or one or more post-operative vision characteristics requested by the patient.

Optical measurement system 1 and the optical measurements obtained therewith may be used intra-operatively, i.e., during a cataract surgery or other surgical procedure, for, e.g., intraoperative eye diagnostics, determining IOL placement and position, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a cap sulotomy, fragmentation or a patient's lens or IOL placement during the cataract surgery. In some embodiments, measurements using optical measurement system 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

Optical measurement system 1 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

Optical measurement system 1, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement system 1, in conjunction with measurement data of a subject's eye obtained by optical measurement system 1, for cataract diagnostics or cataract treatment planning, which may include specifying and/or selecting a particular IOL for a subject's eye. For example, one or more processors of optical measurement system 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement system 1 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and diagnostic system further comprises a memory operable to store Intraocular Lens ("IOL") Data, the IOL data including a plurality of dioptic power, anterior and posterior radius, IOL thickness, refractive index, asphericity, toricity, echelette features, haptic angulation and lens filter.

In many embodiments, the eye imaging and diagnostic system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation and lens filter.

An improved system for selecting an intraocular lens (IOL) for implantation, comprises: a memory operable to store data acquired from each of the corneal topography subsystem, the wavefront sensor subsystem and the Optical Coherence Tomography subsystem, wherein the stored data includes a plurality of ocular biometry information, anterior corneal surface information, posterior corneal surface information, anterior lens surface information, and posterior lens surface information, lens tilt information and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index, asphericity, toricity, echelette features, haptic angulation and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and a IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence.

A method of selecting an intraocular lens (IOL) to be implanted in a subject's eye, comprising: measuring a plurality of eye characteristics comprising ocular biometry information, anterior corneal surface information, posterior corneal surface information, anterior lens surface information, and posterior lens surface information, lens tilt information and lens position information; and for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) modeling the subject eye with the intraocular lens; (2) simulating the subject eye based on the plurality of IOL predetermined parameters and the predicted IOL position; (3) performing a ray tracing and a IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence.

A tangible computer-readable storage device storing computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens tilt information and lens position information; for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) simulating a geometry of the subject eye with each of the plurality of intraocular lenses (IOL) implanted, in accordance with the plurality of eye characteristics; (2) performing a ray tracing and a IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence.

A method of predicting the intraocular lens position comprising: determining a plurality of eye characteristics before cataract surgery, comprising ocular biometry information, anterior corneal surface information, posterior corneal surface information, anterior lens surface information, and posterior lens surface information, lens tilt information and lens position information; determining a plurality of eye characteristics after cataract surgery, comprising ocular biometry information, anterior corneal surface information, posterior corneal surface information, anterior lens surface information, and posterior lens surface information, lens tilt information and lens position information; calculating or measuring, based on a mathematical relationship, a distance from the apex to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex to the plane where the intraocular lens is.

An improved system for planning a refractive treatment of an eye of a patient, the system comprising: a memory operable to store eye measurement data comprising ocular biometry information, anterior corneal surface information, posterior corneal surface information, anterior lens surface information, and posterior lens surface information, lens tilt information and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction of the eye of the patient. The processor may comprise tangible media embodying machine readable instructions for implementing the derivation of the treatment.

An improved method for planning a refractive treatment of an eye of a patient, the system comprises: measuring a plurality of ocular biometry information, anterior corneal surface information, posterior corneal surface information, anterior lens surface information, and posterior lens surface information, lens tilt information and lens position information.

A method of customizing at least one parameter of an intraocular lens, comprising: measuring a plurality of eye characteristics comprising ocular biometry information, anterior corneal surface information, posterior corneal surface information, anterior lens surface information, and posterior lens surface information, lens tilt information and lens position information; determining a desired postoperative condition of the eye; empirically calculating a post-operative condition of the eye based at least partially on the measured eye characteristics; and predictively estimating, in accordance with an output of said empirically calculating and the eye characteristics, with at least one parameter of the intraocular lens to obtain the desired postoperative condition.

A method of adjusting the refractive power in an eye of a patient who has undergone cataract surgery comprising: measuring a plurality of post-operative eye characteristics in an eye of a patient who has previously undergone cataract surgery, the eye characteristics comprising ocular biometry information, anterior corneal surface information, posterior corneal surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure; modeling the subject eye based on the corrective procedure; performing one of a ray tracing and a power calculation based on said eye model; and selecting a corrective procedure from the plurality of IOL models corresponding to the optimized IOL based on a predetermined criteria.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4)

selecting an IOL from the plurality of IOL models corresponding to the optimized IOL based on a predetermined criteria.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereby reference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

I claim:

1. A method, comprising:
   directing laser light from a pupil retro illumination light source onto a retina of an eye via a sample path of an optical coherence tomography (OCT) interferometer of an optical measurement instrument which includes the pupil retro illumination light source and the OCT interferometer, the laser light passing through an intraocular lens (IOL) implanted into the eye;
   capturing an image of the eye from a portion of the laser light returned from the retina of the eye by an iris camera, the returned laser light also passing through the IOL;
   detecting from the captured image one or more fiducials of the IOL; and
   ascertaining an angular orientation of the IOL within the eye from the one or more detected fiducials.

2. The method of claim 1, further comprising employing a wavefront aberrometer of the optical measurement instrument to ascertain a magnitude of astigmatism and a refractive cylinder axis of the eye.

3. The method of claim 2, further comprising ascertaining an angular orientation at which the IOL should have been disposed within the eye to produce optimal vision, from the measured magnitude of the astigmatism of the eye, the measured refractive cylinder axis of the eye, and a known cylinder power of the IOL.

4. The method of claim 1, further comprising employing the OCT interferometer to determine from an OCT measurement of the eye a position of the implanted IOL within the eye.

5. The method of claim 1, wherein the optical measurement instrument further includes a corneal topographer and a structure having an aperture therethrough, wherein all of the wavefront aberrometer, the corneal topographer, the OCT interferometer, and the pupil retro illumination light source direct light to the eye through the aperture.

6. The method of claim 1, wherein the sample path includes a Z-axis telescope, the method further comprising employing the Z-axis telescope to focus an OCT probe beam at a desired depth within the eye.

7. The method of claim 6, wherein the sample path includes a scanner, the method further comprising employing the scanner to scan the OCT probe beam in X and Y directions to span an X-Y OCT measurement space in the eye.

8. The method of claim 2, wherein detecting the one or more fiducials of the IOL from the captured image comprises detecting one or more dark spots in the captured image.

9. The method of claim 1, further comprising operating the OCT interferometer to measure structures within the eye, including:
   emitting a second laser light by a swept laser light source;
   splitting the second laser light by an optical splitter into a first portion and a second portion;
   by the sample path, receiving the first portion of the second laser light, directing the first portion into the eye as an OCT probe beam, receiving a portion of the OCT probe beam back from the eye, and directing the received portion of the OCT probe beam back from the eye to a detector of the OCT interferometer; and
   by a reference path of the OCT interferometer, receiving the second portion of the second laser light and passing the second portion therethrough to the detector;
   by the detector, receiving from the sample path the portion of the OCT probe beam back from the eye, receiving from the reference path the second portion of the second laser light, and in response thereto, outputting an OCT signal having peaks whose relative timing representing a depths of various reflection and scattering surfaces within the eye.

10. The method of claim 9, wherein a wavelength of the second laser light emitted by the swept laser light source is different from a wavelength of the laser light from the pupil retro illumination light source.

11. The method of claim 10, further comprising:
by a wavelength splitting beam splitter, receiving the portion of the OCT probe beam back from the eye and the pupil retro illumination light returned from the pupil, and directing the portion of the OCT probe beam back from the eye to the detector of the OCT interferometer while directing the pupil retro illumination light returned from the pupil to the iris camera.

12. The method of claim 9, further comprising:
scanning the pupil retro illumination light by moving an OCT scan mirror of the sample path of the OCT interferometer in a pattern that causes the pupil retro illumination light to move on the retina such that the pupil retro illumination light returned from the retina fills an entirety of the pupil within an image capture time of a single frame of the iris camera.

13. The method of claim 1, further comprising:
providing an aperture before the iris camera to limit a range of ray angles of light that reaches the iris camera; and
moving the aperture out of a path between the pupil retro illumination light returned from the pupil and the iris camera when the iris camera captures the image of the eye from the pupil retro illumination light returned from the pupil.

* * * * *